US011701488B2

(12) United States Patent
Hazan et al.

(10) Patent No.: US 11,701,488 B2
(45) Date of Patent: Jul. 18, 2023

(54) CATHETER DEVICE AND METHOD OF USING THE SAME

(71) Applicant: INTERVAAL PTE. LTD., Singapore (SG)

(72) Inventors: Yosi Hazan, Misgav (IL); Chee Mun Eric Loh, Singapore (SG); Shan Lu, Singapore (SG); Dotan Tromer, Misgav (IL)

(73) Assignee: INTERVAAL PTE. LTD., Singapore (SG)

( * ) Notice: Subject to any disclaimer, the term of this patent is extended or adjusted under 35 U.S.C. 154(b) by 358 days.

(21) Appl. No.: 16/612,370

(22) PCT Filed: Aug. 3, 2018

(86) PCT No.: PCT/SG2018/050395
§ 371 (c)(1),
(2) Date: Nov. 9, 2019

(87) PCT Pub. No.: WO2019/035761
PCT Pub. Date: Feb. 21, 2019

(65) Prior Publication Data
US 2020/0069911 A1    Mar. 5, 2020

Related U.S. Application Data

(60) Provisional application No. 62/546,245, filed on Aug. 16, 2017.

(51) Int. Cl.
*A61M 25/00* (2006.01)
*A61M 25/10* (2013.01)
*A61B 17/00* (2006.01)

(52) U.S. Cl.
CPC .... *A61M 25/0017* (2013.01); *A61M 25/0075* (2013.01); *A61M 25/10185* (2013.11);
(Continued)

(58) Field of Classification Search
CPC ........ A61M 2025/109; A61M 25/0017; A61M 25/0069; A61M 25/0074; A61M 25/0075;
(Continued)

(56) References Cited

U.S. PATENT DOCUMENTS 3,769,981 A    11/1973    McWhorter
5,466,222 A *  11/1995    Ressemann ........... A61M 29/02
                                                      604/524

(Continued)

FOREIGN PATENT DOCUMENTS

CN        1852747 A      10/2006
CN      106492294 A       3/2017
(Continued)

OTHER PUBLICATIONS

Supplementary European Search Report and Information on Search Strategy for European Application No. EP18846651.
(Continued)

*Primary Examiner* — Adam Marcetich
(74) *Attorney, Agent, or Firm* — JCIP; Joseph G. Chu; Jeremy I. Maynard

(57) ABSTRACT

Disclosed is a catheter device including a proximal tube having a first part of a first lumen; a distal tube having a second part of the first lumen; a second lumen connecting the proximal tube and the distal tube; wherein the connection comprise an area of discontinuity between the first part and second part; wherein the area of discontinuity comprises a support element configured to resist axial movement of the distal tube relative to the proximal tube and vice versa; and wherein the second lumen is arranged to activate or cause at least one obstruction element to restrict the flow of urine from the proximal tube to the area of discontinuity and to restrict the flow of urine from the area of discontinuity to the distal tube.

18 Claims, 17 Drawing Sheets

(52) U.S. Cl.
CPC .............. *A61B 2017/00871* (2013.01); *A61M 2025/109* (2013.01)

(58) Field of Classification Search
CPC ............ A61M 25/10185; A61M 27/00; A61M 2210/1089; A61M 2210/1085; A61F 2/0013; A61F 2/0022; A61F 2/0027; A61F 2/04; A61F 2002/047
See application file for complete search history.

(56) References Cited

U.S. PATENT DOCUMENTS

| | | | | |
|---|---|---|---|---|
| 5,738,654 | A * | 4/1998 | Tihon | A61F 2/04 604/105 |
| 5,876,417 | A * | 3/1999 | Devonec | A61F 2/04 606/192 |
| 6,017,323 | A * | 1/2000 | Chee | A61M 25/104 604/249 |
| 6,093,191 | A | 7/2000 | Porter | |
| 2002/0045886 | A1 | 4/2002 | Porter | |
| 2002/0128705 | A1* | 9/2002 | Devonec | A61F 2/04 623/1.11 |
| 2002/0173741 | A1* | 11/2002 | Rioux | A61F 2/0022 602/41 |
| 2002/0177902 | A1* | 11/2002 | Rioux | A61F 2/04 600/29 |
| 2003/0069647 | A1* | 4/2003 | Desmond, III | A61F 2/95 606/108 |
| 2003/0153899 | A1* | 8/2003 | Eshel | A61M 25/0662 604/102.03 |
| 2004/0044307 | A1* | 3/2004 | Richardson | A61M 25/0017 604/102.01 |
| 2005/0033346 | A1* | 2/2005 | Sater | A61M 25/09025 606/194 |
| 2005/0107735 | A1* | 5/2005 | Lennox | A61F 2/0027 604/9 |
| 2006/0111691 | A1* | 5/2006 | Bolmsjo | A61M 25/0017 604/544 |
| 2008/0172040 | A1* | 7/2008 | Smith | A61M 25/0017 604/544 |
| 2008/0269546 | A1* | 10/2008 | Wilkie | A61F 2/0022 600/29 |
| 2013/0041352 | A1 | 2/2013 | Smith | |
| 2013/0197458 | A1* | 8/2013 | Salama | A61F 5/448 604/335 |
| 2015/0314103 | A1* | 11/2015 | Hannon | A61M 25/0009 53/431 |
| 2018/0161542 | A1* | 6/2018 | Yachia | A61M 25/04 |
| 2018/0353318 | A1* | 12/2018 | Logier | A61F 5/44 |

FOREIGN PATENT DOCUMENTS

| | | |
|---|---|---|
| DE | 4130434 A1 | 3/1993 |
| EP | 0873760 A1 | 10/1998 |
| TW | 422710 B | 2/2001 |
| WO | 0228465 A1 | 4/2002 |
| WO | 02087412 A2 | 11/2002 |
| WO | 2012/059906 A1 | 5/2012 |

OTHER PUBLICATIONS

Chinese Search Report for Chinese Application No. 201880052501.0.

International Search Report and Written Opinions of International Searching Authority for International Application No. PCT/SG2018/05395.

Notice of Reasons for Refusal dated Apr. 12, 2022 from JPO for Japanese Patent Application No. 2020-509471.

\* cited by examiner

CATHETER DEVICE AND METHOD OF USING THE SAME

This application claims the priority to U.S. application No. 62/546,245, filed 16 Aug. 2017, the contents of which are incorporated herein by reference.

FIELD

The present invention relates to a catheter device, and a method associated with the use of the catheter device. The catheter device is particularly suited, but not limited to the reduction of urinary tract infection (UTI).

BACKGROUND

The following discussion of the background to the invention is intended to facilitate an understanding of the present invention only. It should be appreciated that the discussion is not an acknowledgement or admission that any of the material referred to was published, known or part of the common general knowledge of the person skilled in the art in any jurisdiction as at the priority date of the invention.

A urinary tract infection (UTI) is an infection in the urinary system which includes the urethra, bladder and kidneys. According to the US Centers for Disease Control and Prevention (CDC), 1.7 million infections occur in hospitals in the USA annually, resulting in 99,000 preventable deaths. Of these infections, UTI is the most common, accounting for 32% of all healthcare-associated infections resulting in a total cost of US$390-450 million. Catheter associated urinary tract infection (CAUTI) occurs due to the presence of bacteria that "travel" along the catheter causing infection. Among UTI acquired in the hospitals, approximately 75% are associated with a urinary catheter.

An infection may be caused when germs enter the urinary tract. Many of the germs that cause CAUTI are common germs found in intestines that do not usually cause an infection in the urinary tract or bladder. Germs can enter the urinary tract when the catheter is being put in or while the catheter remains in the bladder.

UTIs can affect the bladder (cystitis) and urethra (urethritis).

Despite current solutions, including anti-microbial coatings on urinary catheters, CAUTI remains unabated, particularly since the use of urinary catheter remains high. According to a survey conducted by the National Healthcare Safety Network of the Centers for Diseases Control and Prevention, use of urinary catheter is exceedingly common in healthcare facilities and prevention of CAUTI continues to be an important goal of healthcare infection prevention program.

The pathogenesis of CAUTI relates to the ascending route of infection. This happens through two main mechanisms:

extra-luminally through migration of bacteria along the catheter's surface; or intra-luminally due to colonization of the catheter bag.

In a prospective clinical study, 66% of the infections were extra-luminally acquired and 34% were intra-luminally derived. With the trend to use closed urine collection systems, the rate of intra-luminally acquired infection is reduced but the rate of extra-luminally acquired infection remains high.

Urine plays an important role in UTI prevention as the urine flushes the urethral wall and helps to flush bacteria from the urinary tract. It was recently discovered that bacteria attempt to preserve its position and would grip to the body's cells whenever they feel the force of urine flowing past. When urination stops, this gripping mechanism releases and the bacteria continue its upward movement to other anatomy of the urinary tract. Currently, when a patient is catheterized with a standard urinary catheter, the urethral wall is almost never flushed by urine, as the urine always passes through the catheter, intra-luminally.

Catheters have been designed to reduce UTI. For example, catheters that attempt to combat migration of bacteria with a mid-section that have perforations or a reduced-diameter. Theoretically, urine flowing from the bladder through the perforated or reduced-diameter mid-section washes/flushes the wall of the urethra and washes/flushes away the typical bacteria, to prevent bacteria migration to the bladder, however in practice the mid-sections typically lack the structural integrity for proper insertion into an individual because of structural weaknesses associated with the same, which makes the mid-sections susceptible to inadvertent movement(s) such as folding or ripping during insertion. Such inadvertent movement(s) can cause injury to the urethra and/or the bladder during insertion. Further, urine does not necessarily wash over the wall of all the urethra in the mid-section. Indeed, most of the urine flows straight through the mid-section in the center of the mid-section following the path of least resistance. Accordingly, there may not be sufficient urine flow in the mid-section to reduce or minimize bacteria build-up.

Another problem associated with long term catheterization is that the bladder is kept in a "collapsed form" for a long time. The urine is released constantly at a slow pace. This is necessary because if the urinary tract is obstructed to allow the bladder to fill, it can lead to acute kidney injury (AKI). As such, attempts to obstruct urine flow and fill the bladder require careful monitoring that can add to the cost and risk of AKI. After catheterization, the collapsed bladder needs to be "trained/retained" to expend before sending the patient home. This process might increase hospitalization by a few days as part of training the bladder/patient for normal bladder functionality.

An object of the invention is to ameliorate one or more of the above-mentioned difficulties.

SUMMARY

Aspects of the invention include a method and a catheter device suitable for, but not limited to the minimization or prevention of catheter associated urinary tract infection (CAUTI). The device is an improved catheter designed for prevention of urinary infection. A catheter comprising a urine flow obstruction element, wherein obstruction element may be any element configured to achieve to a temporary closure of urine flow and filling of the urinary bladder, such as a single or multiple clamps, valves, inflatable balloons. The flow obstruction elements may be incorporated at each point along the catheter. The flow obstruction elements can be operated manually or automatically to enable periodical filling and emptying of the urinary bladder configured to mimic biological bladder function in order to minimize risk of infection and acute kidney injury (AKI).

This unique configuration prevents a path for bacteria to migrate from the external urethral orifice to the proximal end and to the bladder.

The inventor(s) has envisaged a catheter device that is able to approximate one or more natural function(s) of a urinary system. The catheter device provides for (a.) a component (also referred to as an obstruction element or urine flow obstructer) for natural build-up of urine in a bladder, and (b.) an opening or open zone (also referred to as an area of discontinuity or a buffer zone) to allow pressurized urine (build up in the bladder) to flow and flush a wall of the urethra when pressurized urine is released via the opening or buffer zone. It is therefore appreciable that the obstruction element functions as a dam and the buffer zone or area of discontinuity provides for a release of pressurized urine to flush the wall of the urethra to reduce or prevent bacterial build up.

The obstruction element may be calibrated depending on the amount of desired pressure to be build-up within the bladder. In some embodiments, the obstruction element may include a valve (one-way or two-way) which is structurally arranged to withstand a predetermined amount of pressure before opening to release the pressurized urine in the bladder. In some embodiments, the obstruction element may include one or more pressure sensors to detect the build-up of the pressure within the bladder to release the urine at a desired time. The calibration may also involve devices having varying shapes, dimensions to achieve the desired timed-release of pressurized urine in the bladder.

The pressure sensors may include mechanical sensors, electrical sensors and/or a combination thereof.

In some embodiments, the obstruction element may be positioned on a proximal lumen of the catheter which when deployed is near a bladder of an individual. In some embodiments, the obstruction element may be positioned on a distal lumen which when deployed is outside the body of an individual.

In some embodiments, the obstruction element may also function as a retaining element which contacts a surface of a urinary bladder when deployed.

It is envisaged to provide a novel urinary catheter that is easily insertable into a patient to mitigate CAUTI by enabling periodic flushing of urethral wall by urine. It is another object of the present invention to provide a mechanism keeping bladder functionality normal through the catheterization period since the urine will be flushed out periodically and not continuously. Moreover, the objective of the catheter of the current invention, is to preserve bladder and urethral functionality, by keeping the urethra flushed with urine with the objective to decrease the ascending migration of bacteria and reduce the rate of CAUTI in urinary catheter through the normal action of urine flushing.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention.

DETAILED DESCRIPTION

Throughout this document, unless otherwise indicated to the contrary, the terms "comprising", "consisting of", "having" and the like, are to be construed as non-exhaustive, or in other words, as meaning "including, but not limited to".

Furthermore, throughout the specification, unless the context requires otherwise, the word "include" or variations such as "includes" or "including" will be understood to imply the inclusion of a stated integer or group of integers but not the exclusion of any other integer or group of integers.

As used in the specification and the appended claims, the singular form "a", and "the" include plural references unless the context clearly dictates otherwise.

Throughout the description, the term 'lumen' and its plural form may be interpreted to include one or more tubes.

Throughout the description, the term 'catheter' and 'catheter device' are used interchangeably.

Throughout the description, the term 'proximal tube' refers to a portion of the catheter which, when deployed in a subject, is relatively near to or within a urinary bladder. The term 'distal tube' refers to a portion of the catheter which has a portion outside the body of the subject.

Throughout the description, the term "preventing catheter associated urinary tract infection" may refer to reducing, minimizing or lessening the presence of a catheter associated urinary tract infection (CAUTI) detected by any signs and symptoms known to a person skilled in the art that provides diagnosis of the CAUTI. It can refer to preventing CAUTI over the timeframe that the catheter is indwelling within a patient or subject. In various embodiments it refers to the absence of CAUTI detected by any signs and symptoms known to a person skilled in the art that provides diagnosis of the CAUTI over the timeframe that the catheter is indwelling within a patient or subject.

As used herein the term "individual", "subject" or "patient" may refer to any individual or organism with a urinary tract system. The subject may include any Gnathostomata or jawed vertebrate, such as mammals, preferably humans.

According to an aspect of the invention there is a catheter device including a proximal tube having a first part of a first lumen configured for urine to flow therethrough; a distal tube having a second part of the first lumen configured for urine to flow therethrough; a second lumen connecting the proximal tube and the distal tube; wherein the connection comprise an area of discontinuity between the first part and second part; wherein the area of discontinuity comprises a support element configured to resist axial movement of the distal tube relative to the proximal tube and vice versa; and wherein the second lumen is arranged to activate or cause an obstruction element to restrict the flow of urine from the proximal tube to the area of discontinuity and to restrict the flow of urine from the area of discontinuity to the distal tube.

Figure 1A:
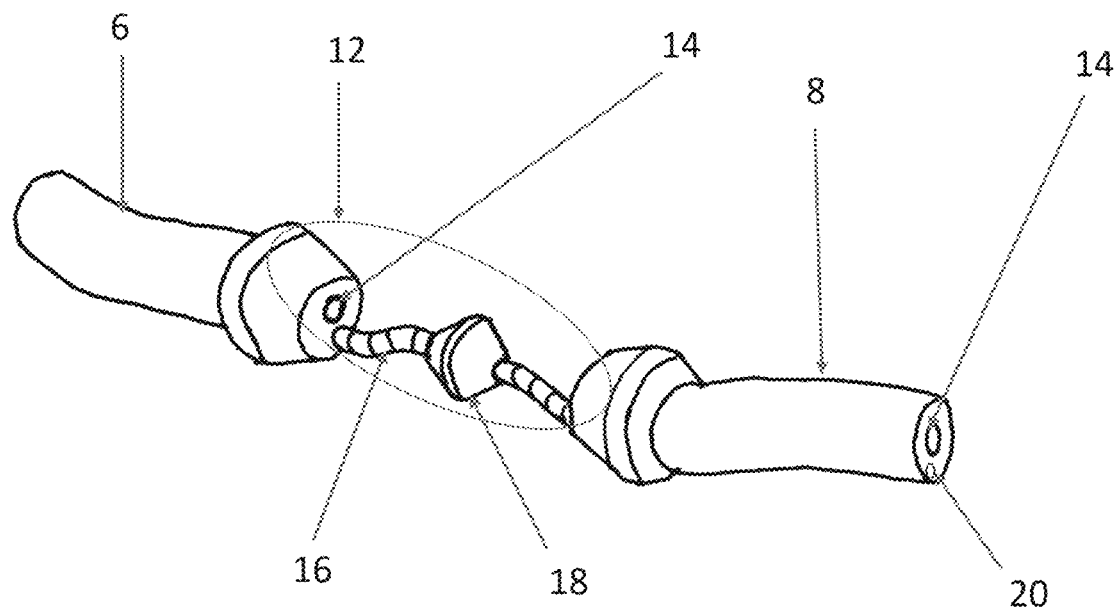
FIG. 1: illustrates various embodiments A, B and C of a catheter device.

Referring to FIG. 1A, an embodiment of the invention shows a catheter device 10 having a proximal tube 6 and a distal tube 8. The proximal tube 6 and distal tube 8 comprise a first lumen 14 for urine to flow therethrough when in use. The first lumen 14 may also be referred to as 'urine lumen', which can be configured to enable the urine to pass through the catheter device 10 into a collecting bag.

The proximal tube 6 and distal tube 8 are connected by a second lumen 16, which in the embodiment is an inflation lumen 16 for inflating one or more obstruction elements. The one or more obstruction element can be in the form of balloons, which when inflated can obstruct urine flow through various part of the first lumen 14. The first lumen 14 may comprise two parts, the first part 14a and the second part 14b. The first part 14a and second part 14b are discontinued or disjointed to form an area of discontinuity 12. The area of discontinuity is also referred to as buffer zone 12. The proximal tube 6 and distal tube 8 are joined only by the second lumen 16.

To provide structural rigidity to the second lumen 16 as well as in the area of discontinuity 12, one or more support elements 18 may be disposed around the proximity of the second lumen 16 to support the second lumen 16. The support element 18 may be in various shapes and sizes and configured to resist axial movement of the distal tube relative to the proximal tube and vice versa.

The support element 18 is arranged to provide suitable strength and flexibility to withstand unnecessary movement of the distal tube 8 relative to the proximal tube 6 and vice versa during deployment of the catheter device 10 into a body of a subject. In particular, during insertion the support element 18 is operable to transmit the axial compression forces to prevent unnecessary movements within the body such as, but not limited to buckling, kinking or bending.

In the embodiment shown in FIG. 1A, the support element 18 is in the form of a bead. The single tube in the inflation lumen 16 also provides the structural strength for axial compressive forces during insertion. It may be flexible enough to go around bends and prevent buckling or kinking.

Figure 1B:
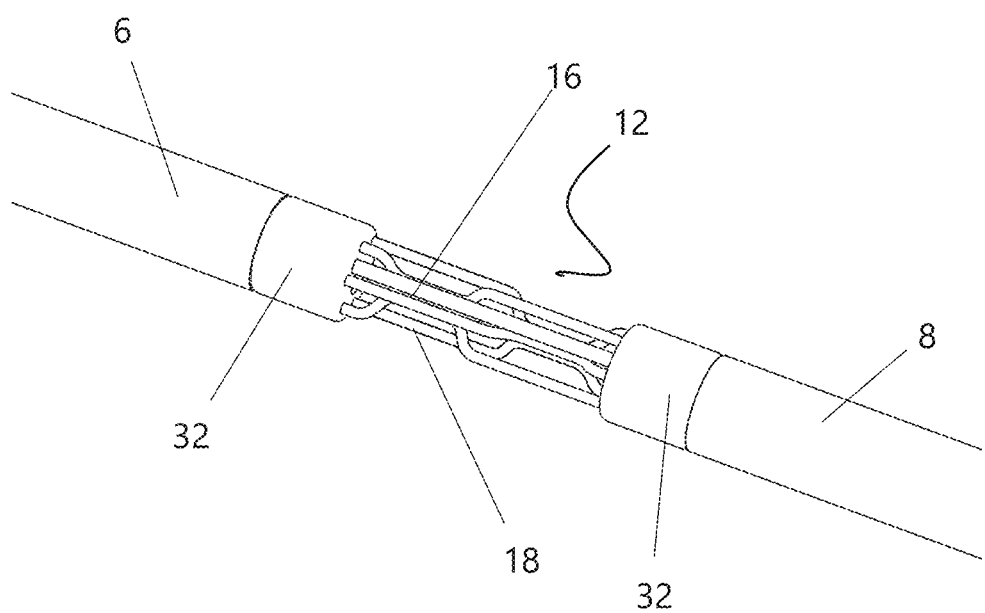
Figure 1C:
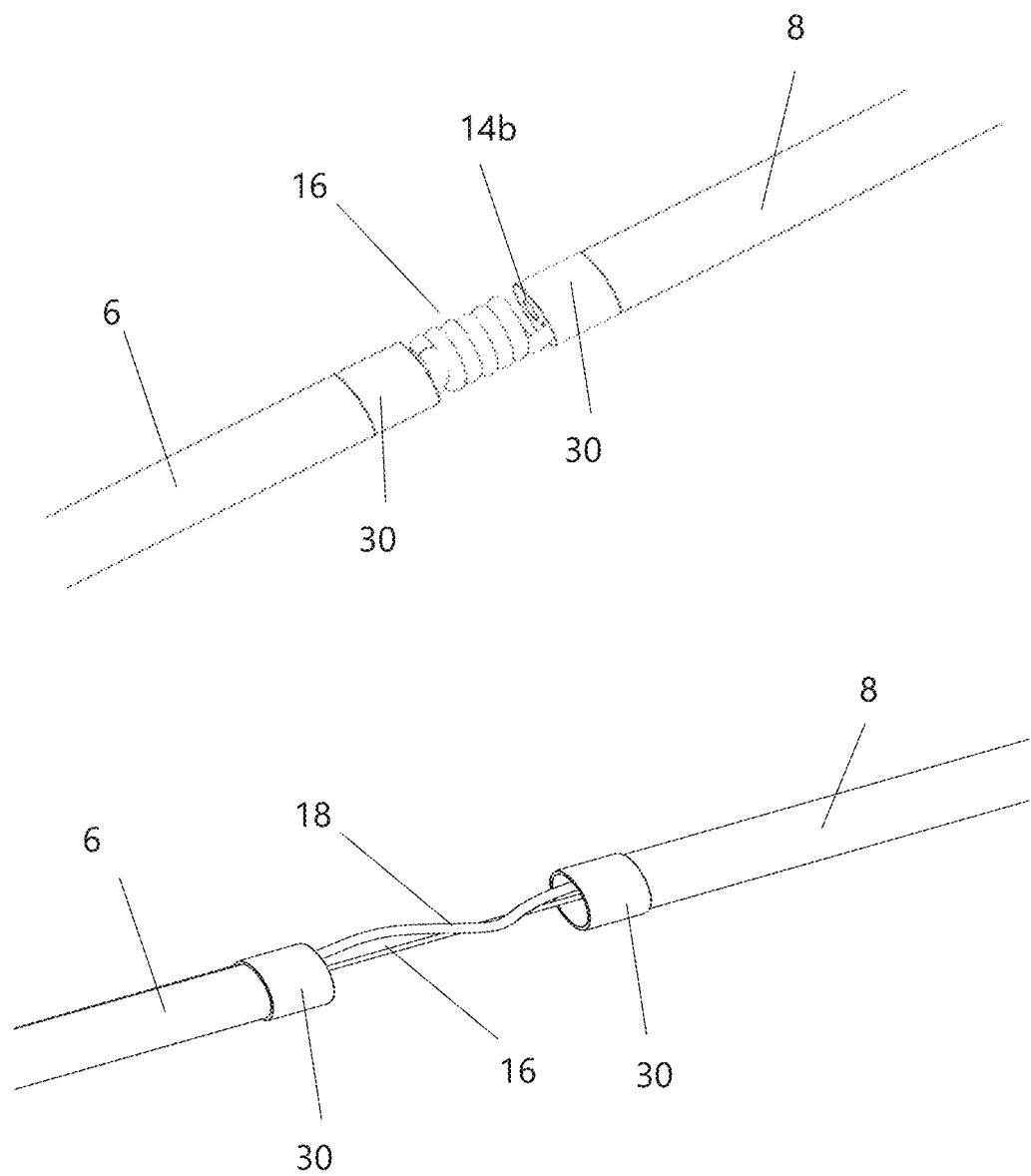

In the embodiment shown in FIG. 1B, the support element 18 comprises a plurality of elongated structures, such as wires or tubes. In some embodiments the elongated structures may be a plurality of wires, which in turn may be elastic to prevent buckling during use. In particular, the plurality of wires comprise nickel titanium alloy, or cobalt chromium alloy.

In the embodiments the nickel titanium alloy comprises nitinol, wherein the nickel and titanium are in almost equal portions.

Figure 10:
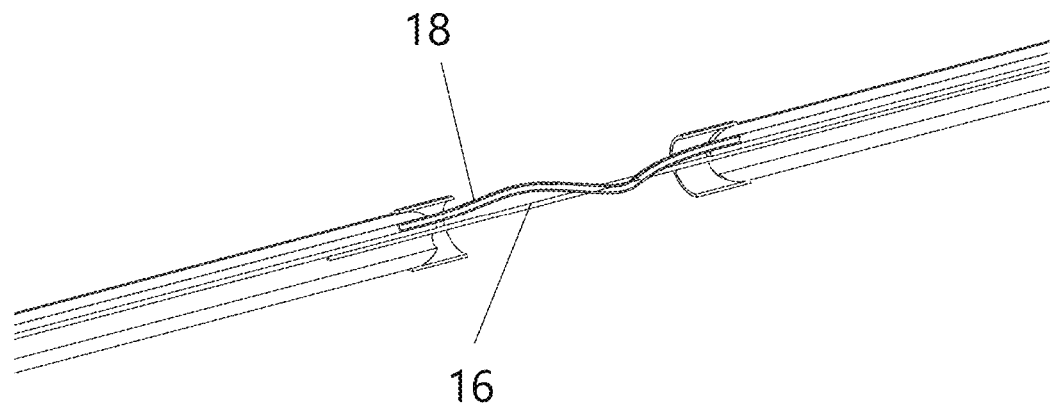

In the embodiment shown in FIG. 10, the buffer zone 12 is covered by a removable cover 30. The connector cover 30 advantageously minimizes any potential damage to the delicate tissues within the urethra and can facilitate passage through the urethra. In addition, the connector cover 30 can also enhance the structural rigidity of the buffer zone 12.

In the embodiment shown in FIG. 10 the connector cover 30 may comprise multiple parts or there may be multiple connector covers 30. In an embodiment, there comprises a distal connector cover on the end of the distal tube adjacent the buffer zone and a proximal connector cover on the end of the proximal tube adjacent the buffer zone.

In various embodiments the connector cover(s) 30 are made from flexible and compliant material to minimize injury to the subject. In various embodiments the connector covers 30 also reduce friction by having a small diameter tip that gradually increase to the diameter of the catheter. This shape has the advantage of minimising any potential damage to the delicate tissues within the urethra and facilitate passage through the urethra.

In various embodiments the connector cover(s) 30 is made of a thermoplastic elastomer formed of linear block copolymers. In various embodiments the linear block copolymers are composed monomers of alternating polarity. In various embodiments the thermoplastic elastomer is thermoplastic polyurethane TPU. In various embodiments the TPU linker is polyether which increases the antibacterial properties of the TPU. In various embodiments the connector cover is formed of a biodegradable material.

The embodiment of FIG. 10 comprises two configurations, a first insertion configuration and a second retention configuration, wherein in the first insertion configuration the proximal tube and the distal tube are in closer proximity than in the second retention configuration. The first insertion configuration may correspond to the state when the catheter is pre-used, on the shelf, or during insertion into a body portion of the subject. The second retention configuration corresponds to the position when the catheter is deployed for use. As is appreciable, in the insertion configuration, the support element 18 and/or inflation lumen 16 is in a 'coiled' state. In such configuration, the support element 18 and/or inflation lumen 16 is shaped like a wound up spring. In the retention configuration, the support element 18 and inflation lumen 16 are 'extended', and the buffer zone 12 is exposed and at a deployed position.

The embodiment of FIG. 10 minimizes the length of the buffer zone 12 during insertion of the catheter device 10 so as to reduce axial force(s) applied during the insertion of the catheter device 10 on the buffer zone 12 but maximizing the length of the buffer zone 12 after proper insertion and when in use to facilitate sufficient washing/flushing of the urethral walls 11 in the region of the exposed buffer zone 12.

In the embodiments of FIGS. 1A, 1B and 10 the buffer zone 12 can include the inflation lumen 16 connecting the proximal tube 6 and the distal tube 8. The inflation lumen 16 is shaped and dimensioned to receive a fluid (e.g. air or saline solution) for inflating an obstructing element a balloon to inflate the balloon to an expanded configuration. In such embodiments the inflation lumen 16 is rigid enough to allow the transmission of axial forces applied during the insertion of the catheter whilst being flexible and compliant enough to bend around obstacles and the natural curves of the urethra and bladder. The inflation lumen 16 is also sufficiently strong enough to withstand breakage, kinking and buckling under the normal forces during intended use.

Figure 2:
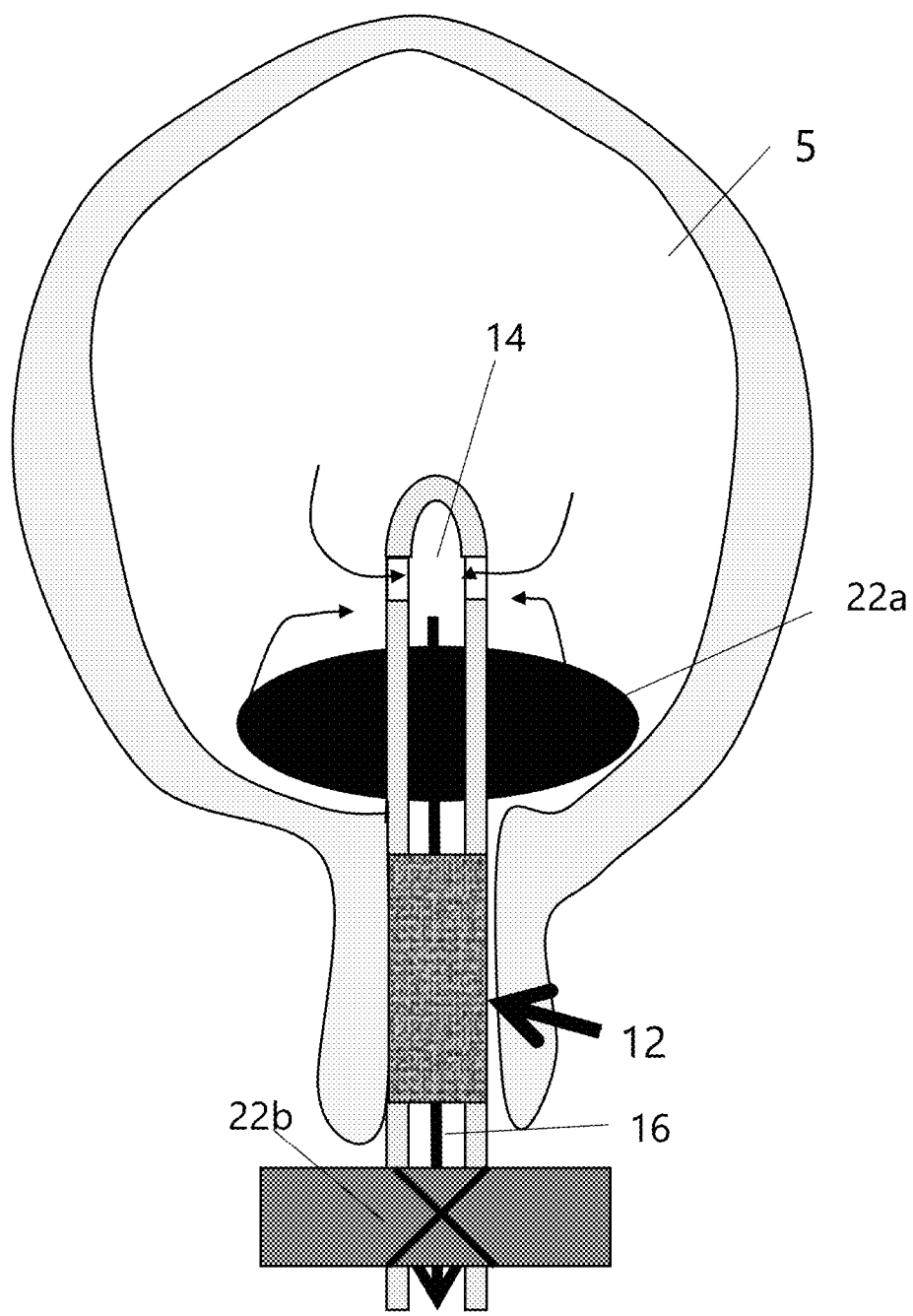
FIG. 2: is a schematic illustration of a catheter device being deployed in a body portion according with some embodiments.
Figure 3:
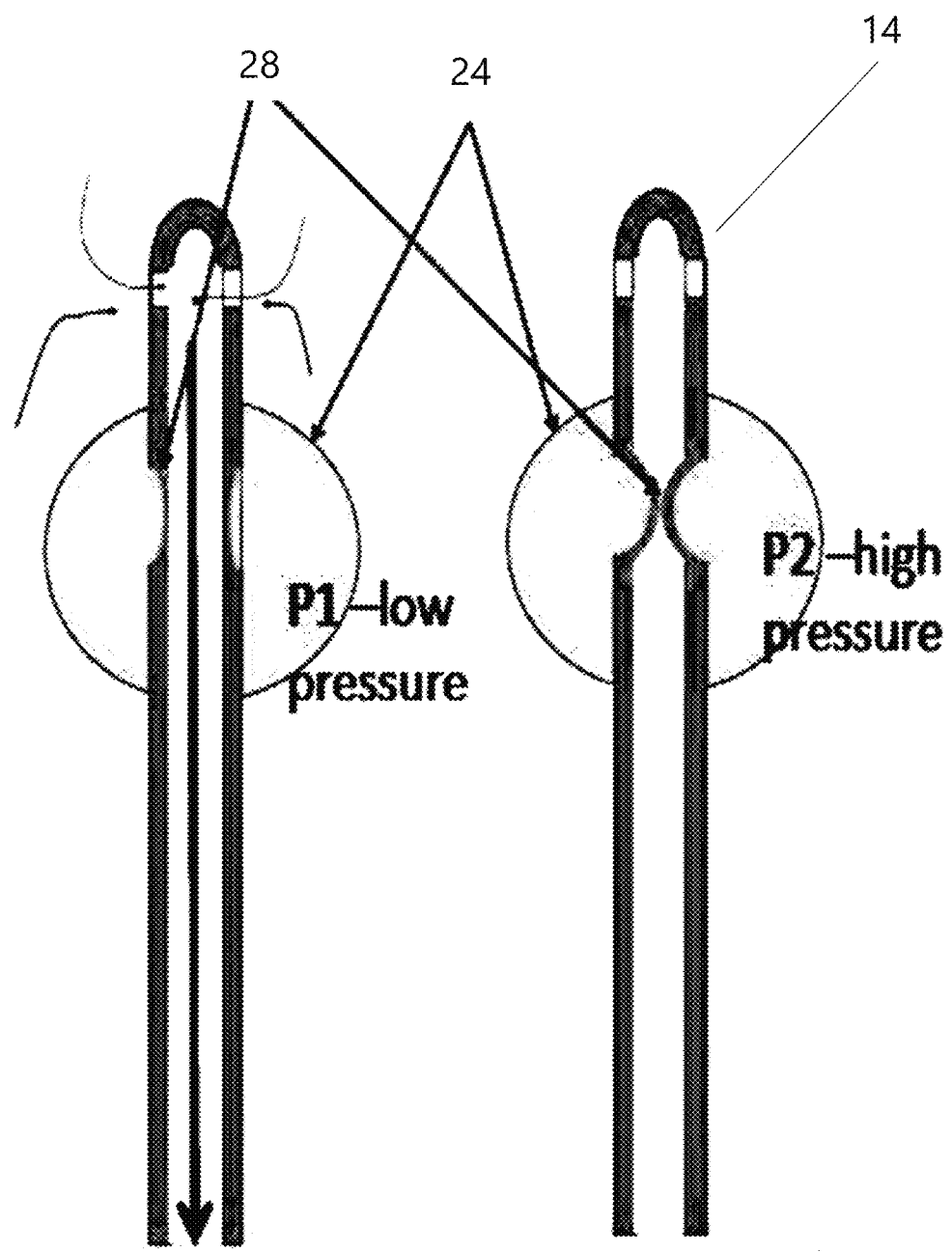
FIG. 3: is a zoom-in of a proximal tube/part of the catheter device and obstruction element in the form of balloon(s) when in use, to generate a high pressure build-up of urine according with some embodiments.

FIG. 2 illustrates a catheter 10 deployed in a subject's body portion, such as a subject's bladder region. When deployed, the proximal tube 6 allows for urine to flow pass and the inflation lumen 16 provides a conduit for inflating one or more obstruction element 22 for pressure build-up of urine at various portions along the catheter device 10. As shown in FIG. 2, there are two obstruction elements 22 deployed along the catheter device 10. A first obstruction element 22a, which can be a balloon, can be positioned at the proximal tube 6, and the second obstruction element 22b, which can be a valve or a clamp, can be positioned at the distal tube 8. FIG. 3 illustrates how an obstruction element 22 works to constrict the walls of a urine lumen 14. In the balloon-type obstruction element 22, inflating the balloon, which is arranged to surround an inner wall of the proximal or distal tube, can simultaneously constrict the walls of the urine lumen.

In use, the buffer zone 12 or area of discontinuity is configured for periodic urine flushing via the periodic activation of the obstruction element(s). Since bacteria or biofilm tend to "cling on" to cells, the physiological process of urine flushing facilitates the bacteria to be flushed off and hence reduce or eradicate bacteria build up. The buffer zone 12 in combination with the urine obstruction element 22 allows suitable pressure build-up of urine prior to periodic opening of the obstruction element 22 to wash/flush flow urine out of the urinary bladder 5, enabling urine to wash the urethral walls 11 surrounding the buffer zone 12 with a suitable force (caused by the build-up pressure) to minimize CAUTI.

In other words, the obstruction element 22 is configured to achieve temporary closure of urine flow and filling of urinary bladder to build urine volume and/or pressure inside the urinary bladder 5, alternated with temporary opening of the urine obstruction element 22 to allow flow of pressurized urine periodically to flush flow urine out of the urinary bladder 5, enabling urine to be in contact with the urethral walls 11 surrounding the buffer zone 12.

The catheter device 10 is an improvement over prior art and is especially suited, but not limited to the prevention of catheter associated urinary tract infection (CAUTI).

In various embodiments the closed end of the proximal tube 6 is rounded to facilitate passage through the urethra during insertion and to minimize any potential injury/damage to the delicate cell tissues within the urethra.

Figure 4A:
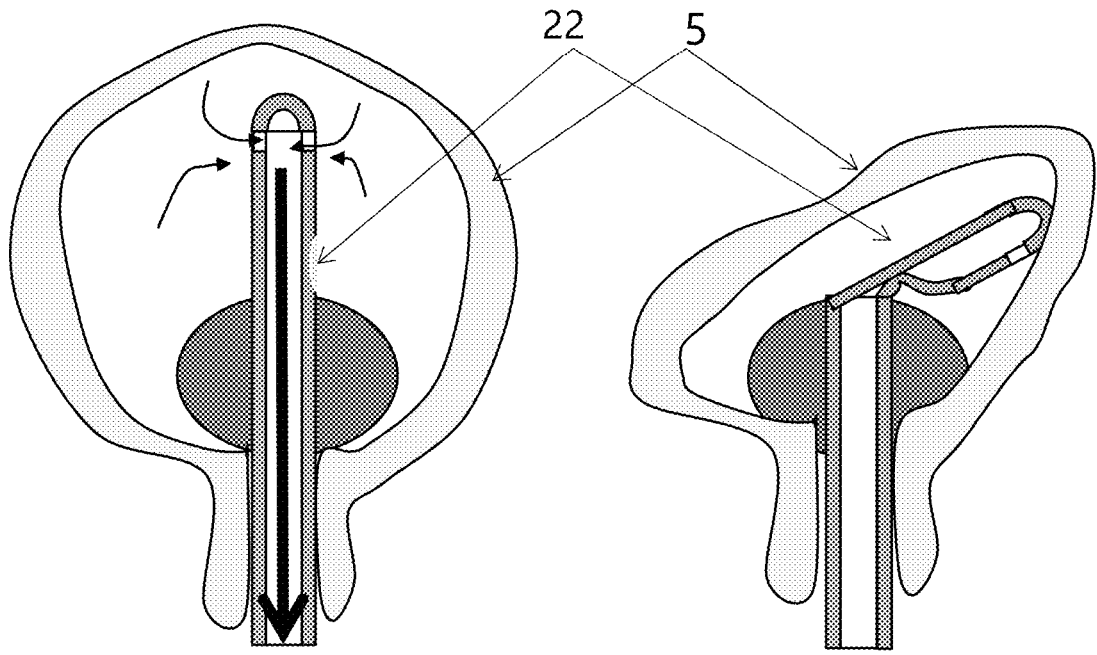
FIG. 4A and FIG. 4B: illustrates opened and closed states of the proximal part of the catheter device automatically depending on a bladder state, according with some embodiments.
Figure 4B:
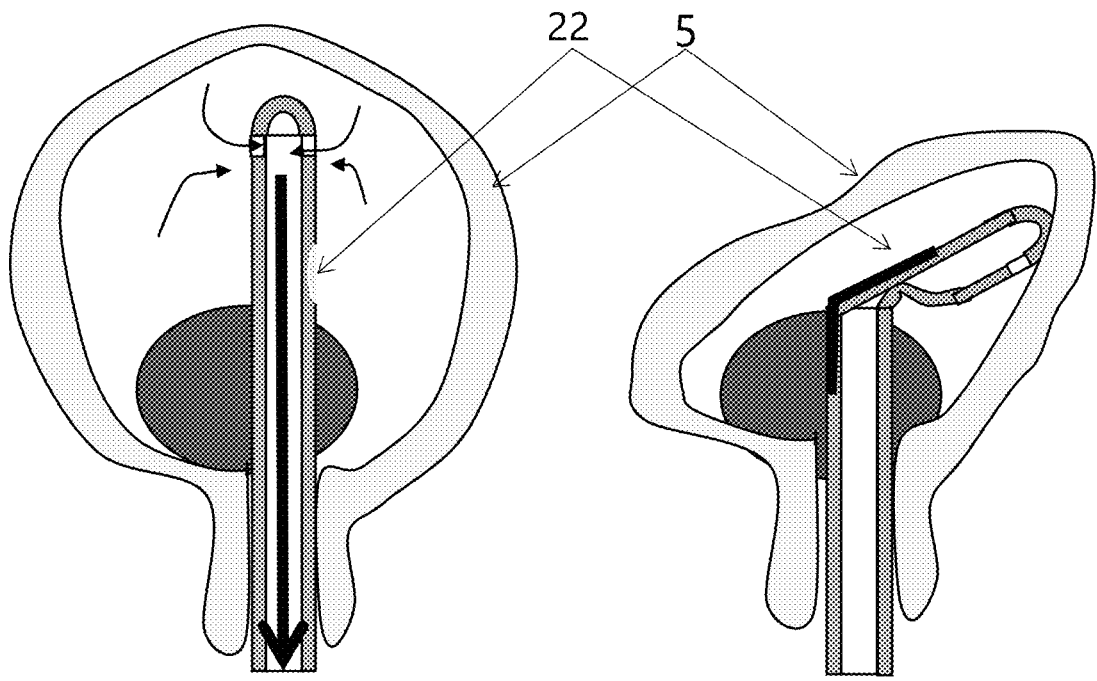

FIG. 4 shows an embodiment where the catheter device 10 is deployed in a urinary bladder. In the embodiment shown in FIG. 4, a catheter having obstruction element 22 is deployed around or at the proximal tube 6. The obstruction element 22 is in the form of a kink. Options for the kink elements include one or more balloon(s) located asymmetrically, and additional spring will be inserted at the tube wall for improved geometrical and time behavior. The spring and the asymmetrically located balloon will have the advantage of making a portion (which can be formed of a different material relative to the rest of the catheter device 10) on the proximal tube more responsive to the obstruction element 22 but will still facilitate the normal functionality of the urinary bladder and urinary tract system when the catheter device 10 is deployed. In various embodiments a weakened portion (kink) on the proximal tube adjacent the inlet configured for narrowing to a block state, wherein the proximal tube buckles and narrows at the weakened portion to close the proximal lumen when the urinary bladder is in a collapsed state during use. In the embodiment shown in FIG. 4B, the proximal tube 6 further comprises a resilient element, such as a spring, located on the proximal tube 6 opposite a weakened portion and an expandable collapsible member around the proximal tube 6, wherein when the expandable collapsible member is expanded a portion of the expandable collapsible member on one side of the proximal tube is proportionately larger than an opposite portion of the expandable collapsible member on an opposite side of the proximal tube (i.e. asymmetrical position).

The combination of the urine obstruction element and the buffer zone work in tandem to achieve an effect most similar to the natural urinary bladder and urinary tract system function. The natural pressure in the bladder effects whether or not the urinary bladder will be emptied. This has the advantage of essentially retaining the normal functionality of the urinary bladder and urinary tract system.

Figure 5:
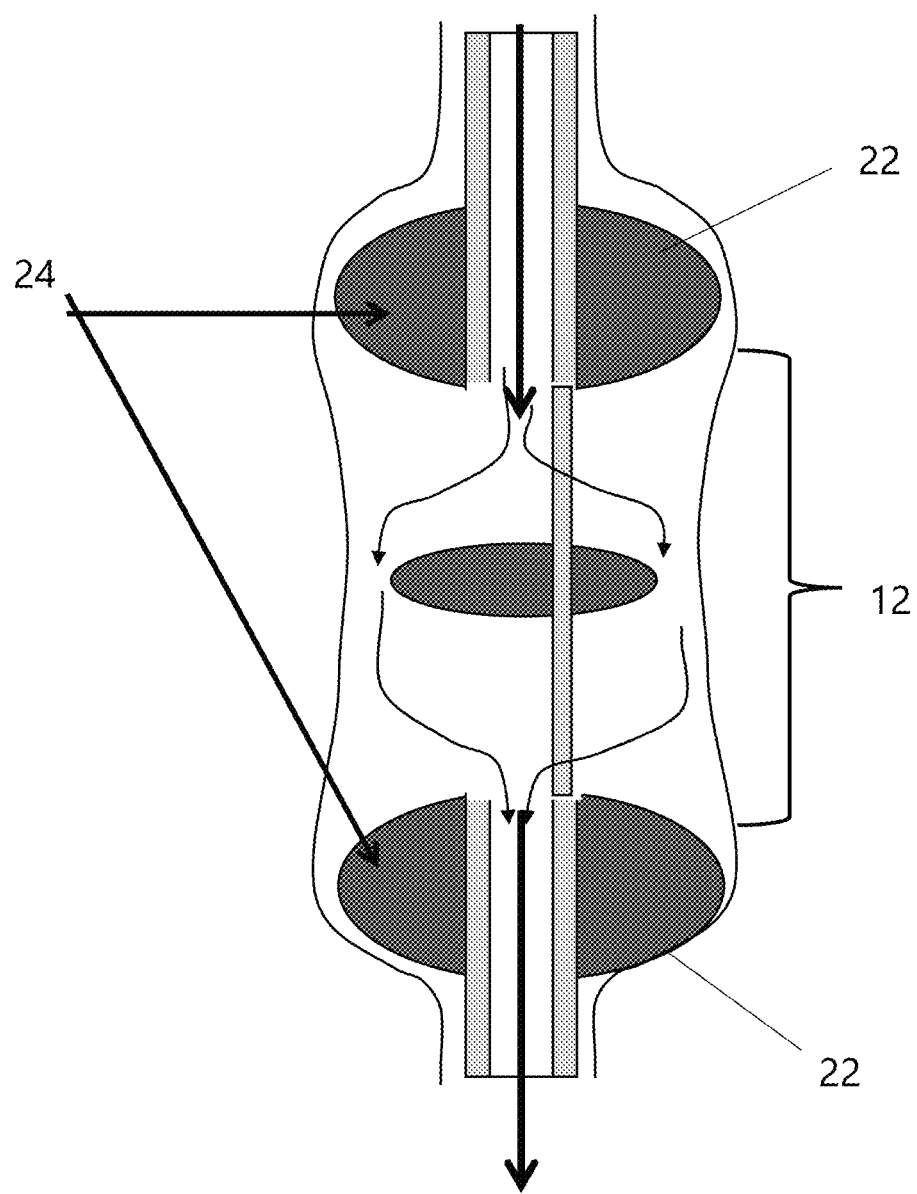
FIG. 5: illustrates a catheter deployed in a body with emphasis on an opening or buffer zone.

FIG. 5 illustrates various zones form by the operations of the obstruction element 22 and the buffer zone 12. In the embodiment of FIG. 5, the sealing zones 26 are formed by obstruction elements 22 in operations. Build-up of urine in the proximal tube 6 and the distal tube 8 forms sealing zones 26. When sufficient pressure is built-up, the urine is released to the buffer zone or the area of discontinuity 12, the pressure build-up facilitates the contact of urine on the urethral walls so as to flush the same. Although the urine lumen 14 of the catheter device 10 is discontinuous, the structural integrity of the buffer zone 12 is maintained by the inflation lumen 16 and the support element 18.

Figure 6:
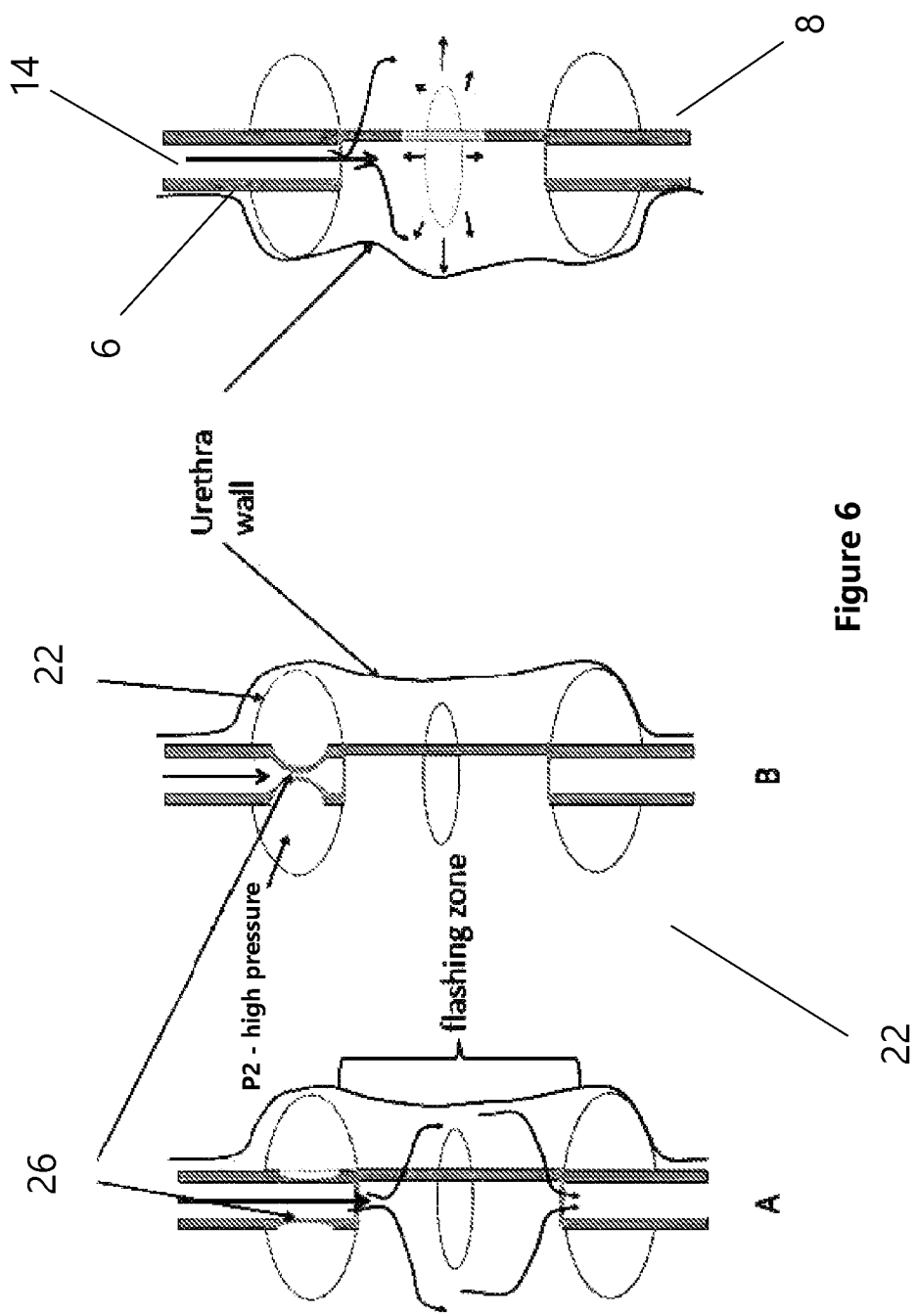
FIG. 6: illustrates a flow of urine along the buffer zone in use to flush the urethral walls.

FIG. 6 illustrates how the sealing zones 26 in the proximal tube 6 can be created by the constriction of the walls of the urine lumen 14 by the obstruction element 22. It is appreciable that constriction of the walls create area of high pressure which can minimize or completely stop the flow of urine around the sealing zones 26. The obstruction element 22 can be a noncompliant balloon, or a central bead functioning as a sealing element.

Figure 7A:
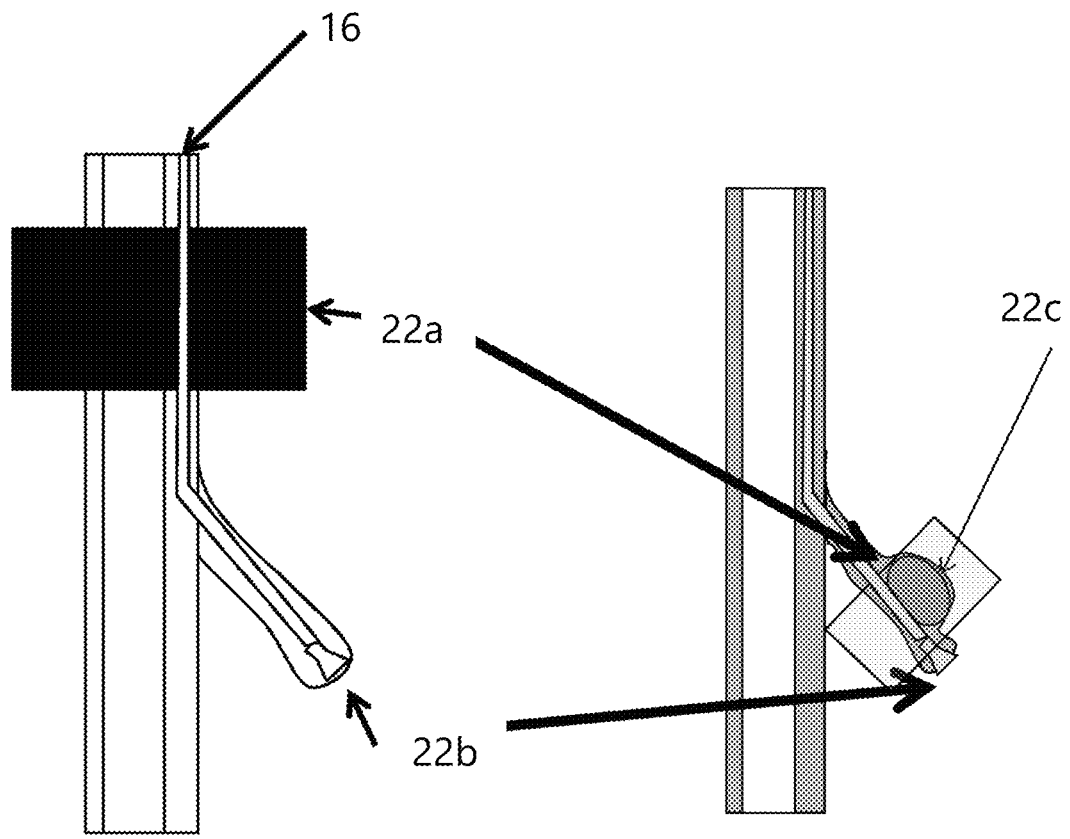
FIG. 7: illustrates a closure of the distal tube/part of a catheter device according to an embodiment of the present invention.
Figure 7B:
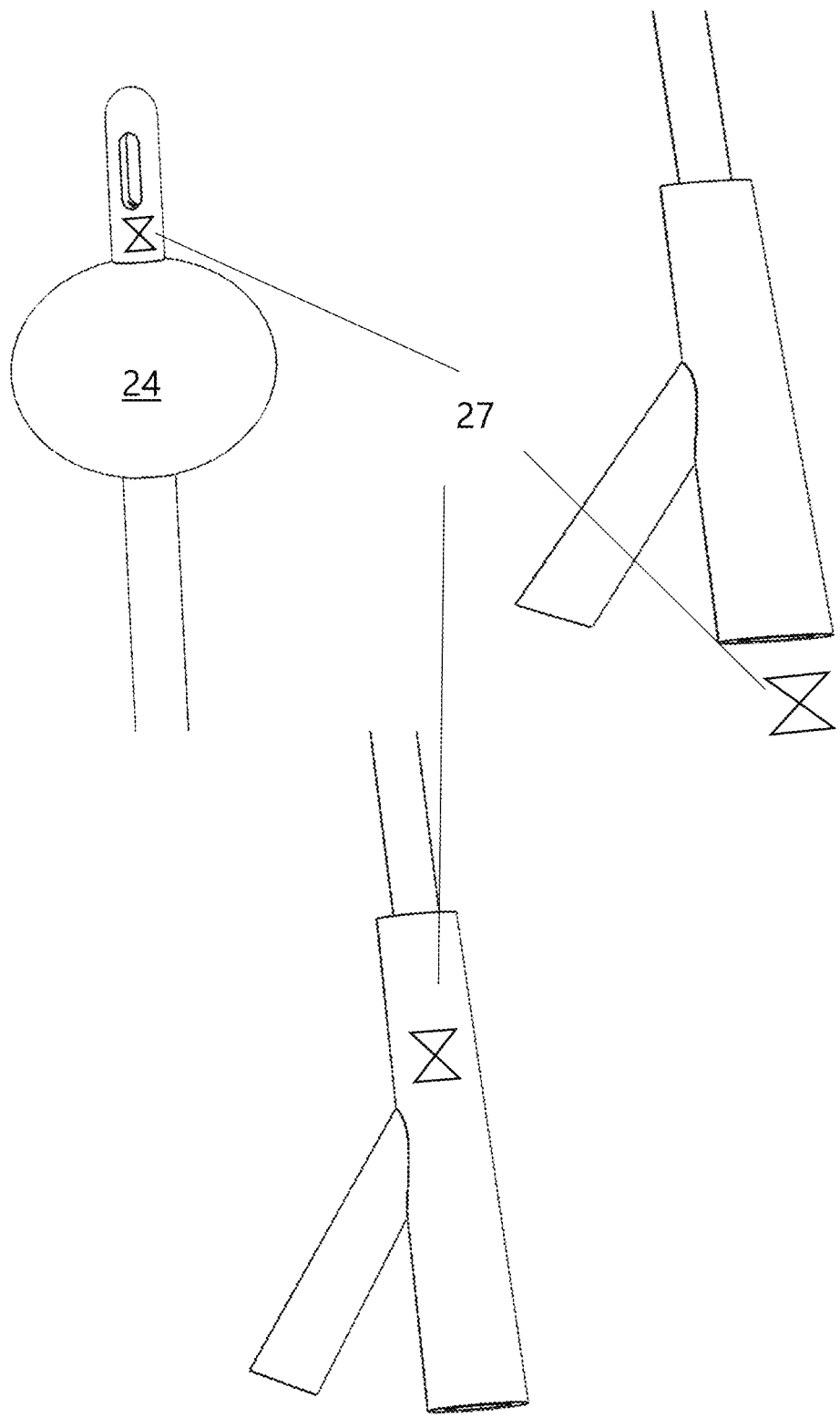

FIG. 7 illustrates another embodiment of the distal tube 8 and the arrangement of the obstruction elements 22. In the embodiment, an obstruction element 22 in the form of a clamp 27 is positioned around an area of the distal tube 8 relatively nearer to the area of discontinuity or buffer zone 12. Another obstruction element 22 may be positioned outside the body of the subject for creation of another sealing zone. It is appreciable that various arrangements and control mechanism (not shown) may be possible to activate clamp 27 and obstruction element 22 concurrently, simultaneously, sequentially, or in other combinations or ways as known to a skilled person.

It is appreciable that in the various embodiments described, the inflation lumen 16 traverses a portion of the distal tube 8 adjacent the buffer zone 12, the buffer zone 12 and the proximal tube 6 to an retaining element 24 (such as an expandable collapsible member) surrounding the proximal tube 6, the expandable collapsible member 24 operable to retain the inlet of the proximal tube within the urinary bladder when the expandable collapsible member 22 is inflated.

Figure 8:
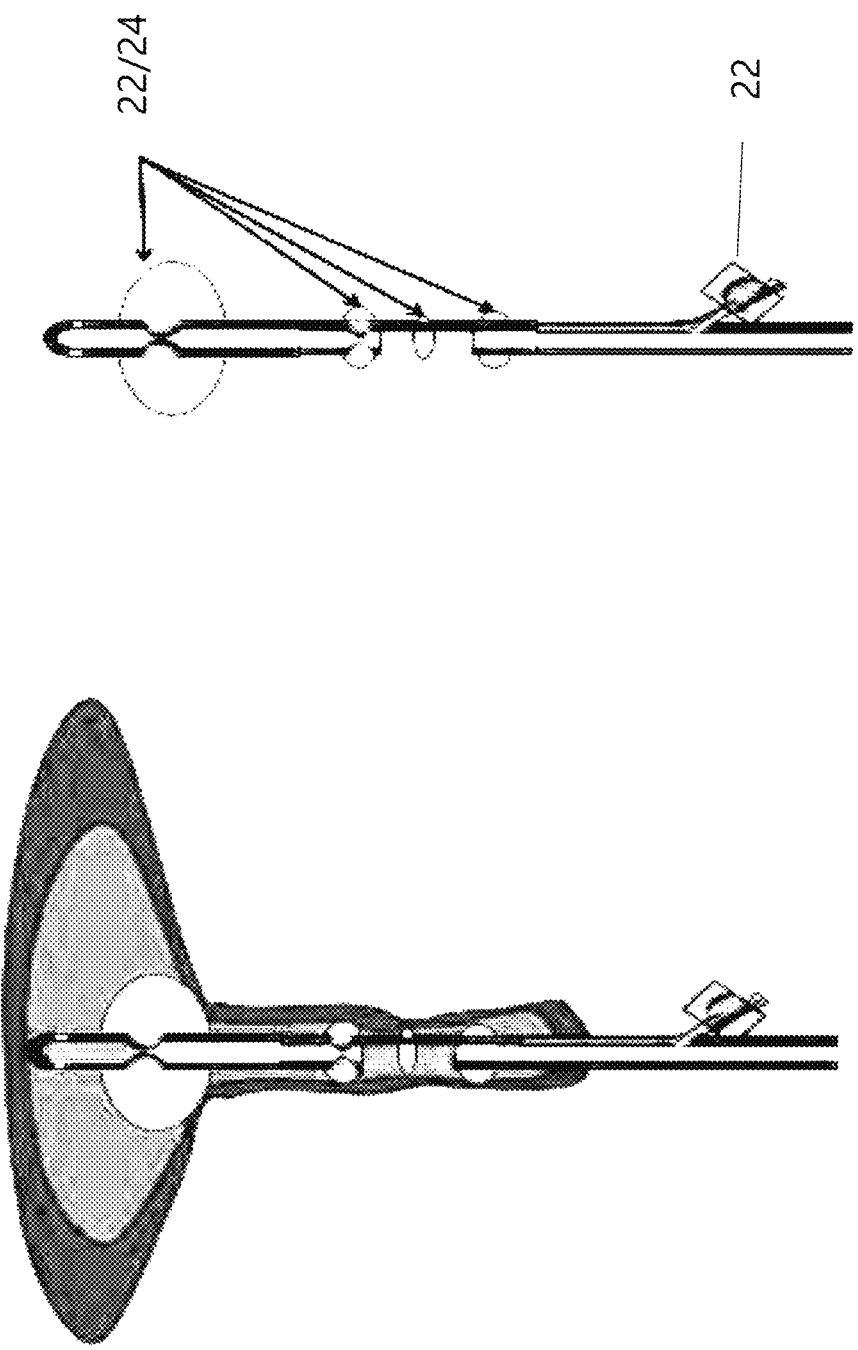
FIG. 8: illustrates a deployed catheter device with sealing elements/valves in operation at various positions along the catheter device for build-up of urine.

FIG. 8 shows various embodiments where the obstruction element 22 may comprise a plurality of balloons. The number of balloons can be two, three, four or five balloons. Inflatable balloons in an expanded state may have the advantage of preventing the collapse of the urethra in use and assure a passage for adequate urine flow, further they can seal the urethra particularly within or below the buffer zone 12 for preventing urine leakage outside the urethral orifice and will allow urine to be effectively collected from the buffer zone 12 into the distal urine lumen. In the embodiment shown in FIG. 8, the balloons can function as both obstruction element 22 and retaining element 24.

Figure 9:
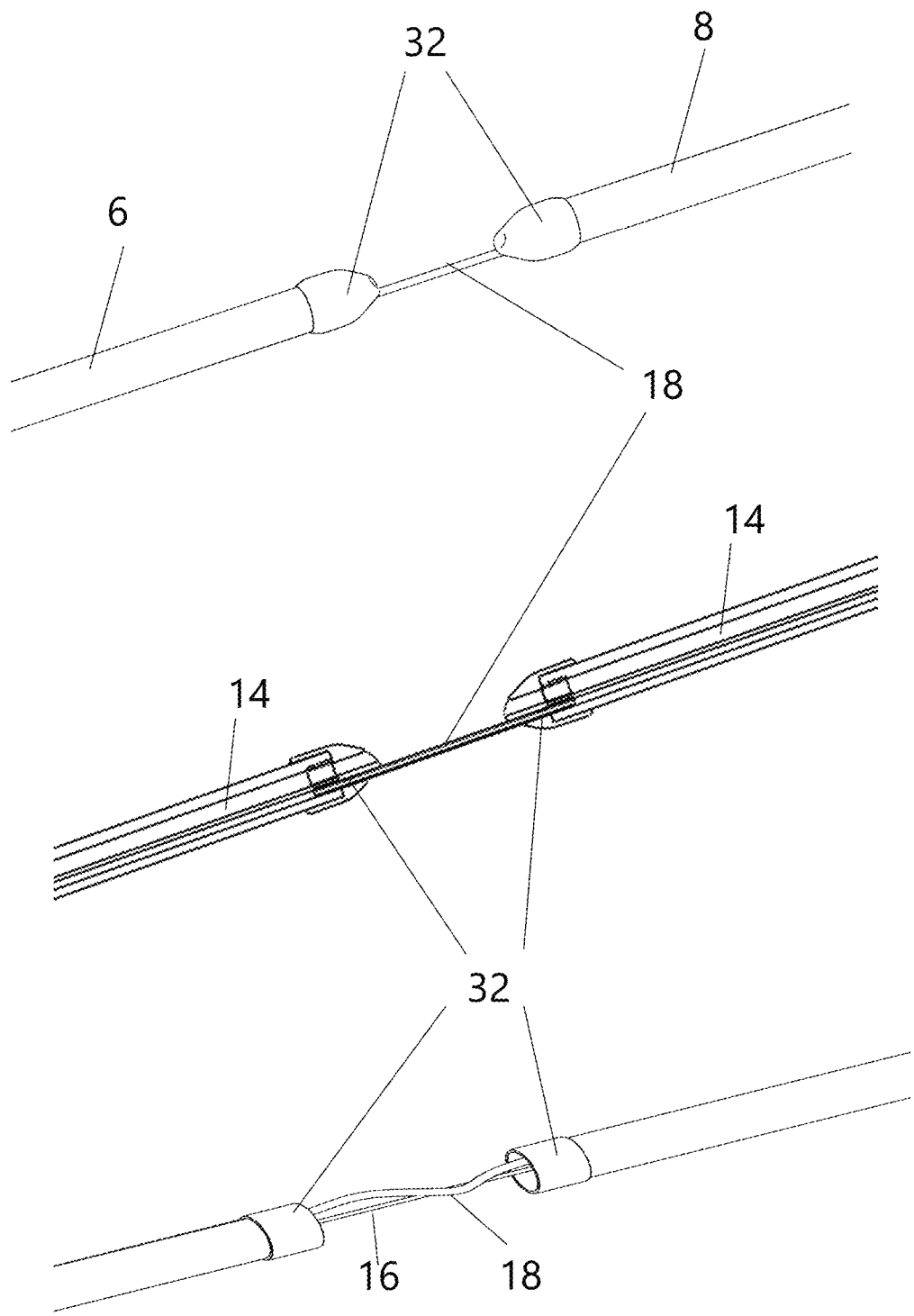
FIG. 9 to FIG. 11 illustrate possible embodiments of an opening or buffer zone at a connection between the proximal and distal tubes of the catheter devices.
Figure 11:
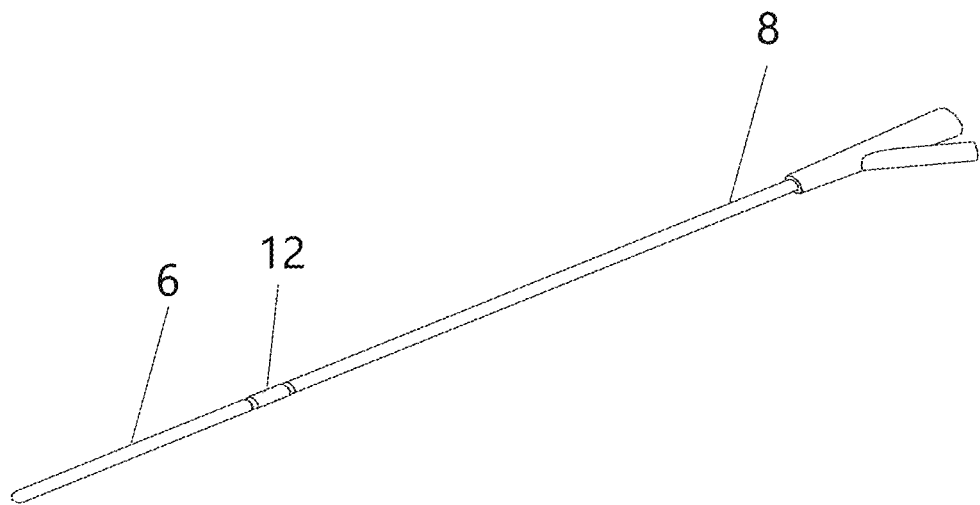

FIGS. 9 to 11 show further details of the catheter device 10 of FIG. 10, in particular in relation to the connector cover 30. The connector cover 30 comprises a sheath 32 enclosing the buffer zone 12 in the first insertion configuration. In various embodiments the sheath 32 is removably attachable.

In various embodiments the sheath 32 comprises one or more weak spots formed via perforations. The sheath 32 may also be design to weakly attached to one of either the proximal tube 6 or the distal tube 8 via latches or flanges (not shown). Such a weak attachment enables the sheath 32 to be released or break apart when the distal tube 8 is pulled forcibly, exposing the buffer zone 12 by longitudinally extending the distance between the proximal tube 6 and the distal tube 8 bridged or connected by the inflation lumen 16 which is uncoiled in the process.

The sheath 32 of the catheter device 10 can flush with the outer surface of the catheter. This has the advantage of minimising any potential damage to the delicate tissues within the urethra and facilitate passage through the urethra. The inflation lumen 16 can be longitudinally extended by being pulled stretched or slid out to enable an action step for deploying the buffer zone 12 upon placing the catheter in position.

In some embodiments the buffer zone 12 may already be in a configuration where it will be used having the sheath 32 covering the buffer zone 12, wherein the sheath can be removed prior to use. In this embodiment the sheath 32 or connector cover 30 surrounds the inflation tube 16 in the use configuration covering the buffer zone 12 to provide a smoother outer surface which is the same or close to the diameter of the catheter. This has the advantage of minimizing any potential damage to the delicate tissues within the urethra and facilitate passage through the urethra. In various embodiment, the removable sheath 32 may cover and/or hide the buffer zone 12 to further reduce risk of injuries caused by thin tubing such as the inflation lumen. In various other embodiments the sheath 32 is attached to a tether line which is run through the urinary lumen. The user will tug this line to break the sheath and pull it out through the said lumen to dispose of the sheath prior to allow urine flow.

Figure 12A:
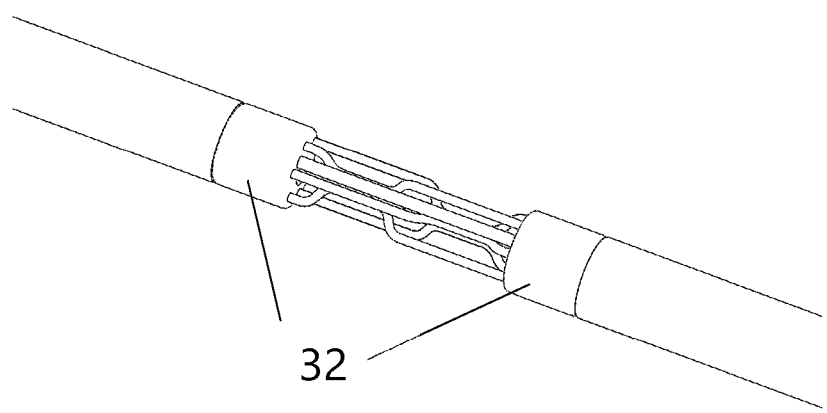
FIGS. 12A and 12B: illustrate a suitable position of an opening or buffer zone along the length of the catheter device according to some embodiments.
Figure 12B:
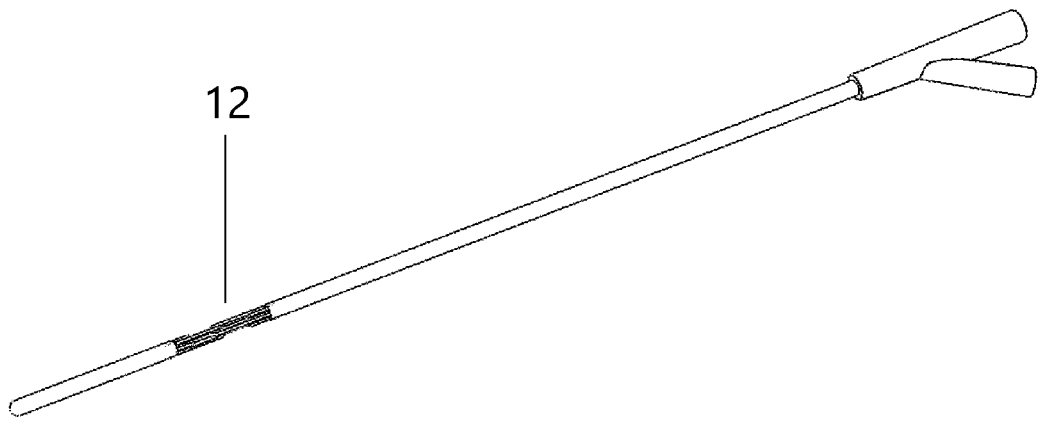

FIG. 12 shows the catheter device 10, connector 30 and/or sheath 32 utilized in the embodiment depicted in FIG. 1B, where the support element 18 comprises a plurality of wires. The connector 30 and sheath 32 may flush with the outer surface of the catheter device 10.

Figure 13:
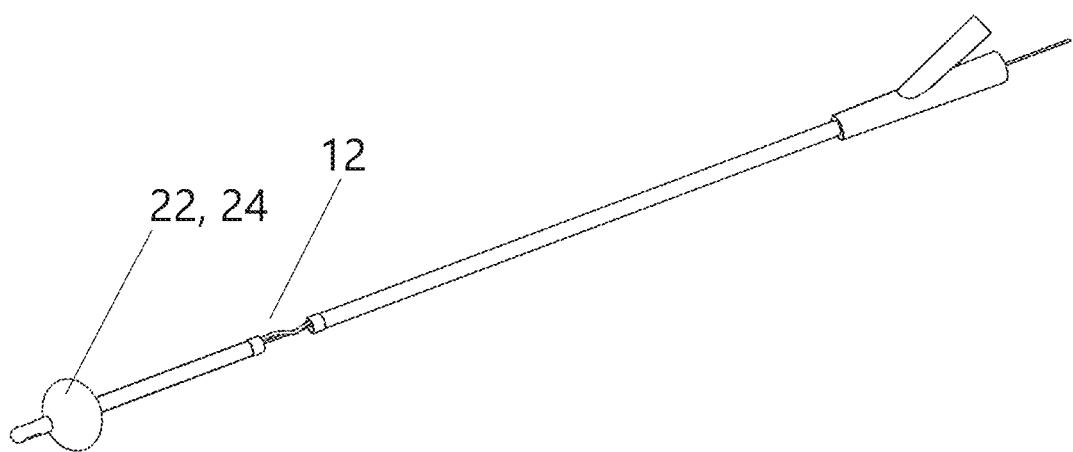
FIG. 13: illustrates possible locations of the obstruction element(s) in the form of pressure relief valves along various positions along the catheter device.

FIG. 13 depicts an embodiment of a catheter device 10 deployed wherein an inflatable balloon functions as a retaining element 24 and a valve (one way or two ways) function as a obstruction element 22 to create a sealing zone.

Figure 14:
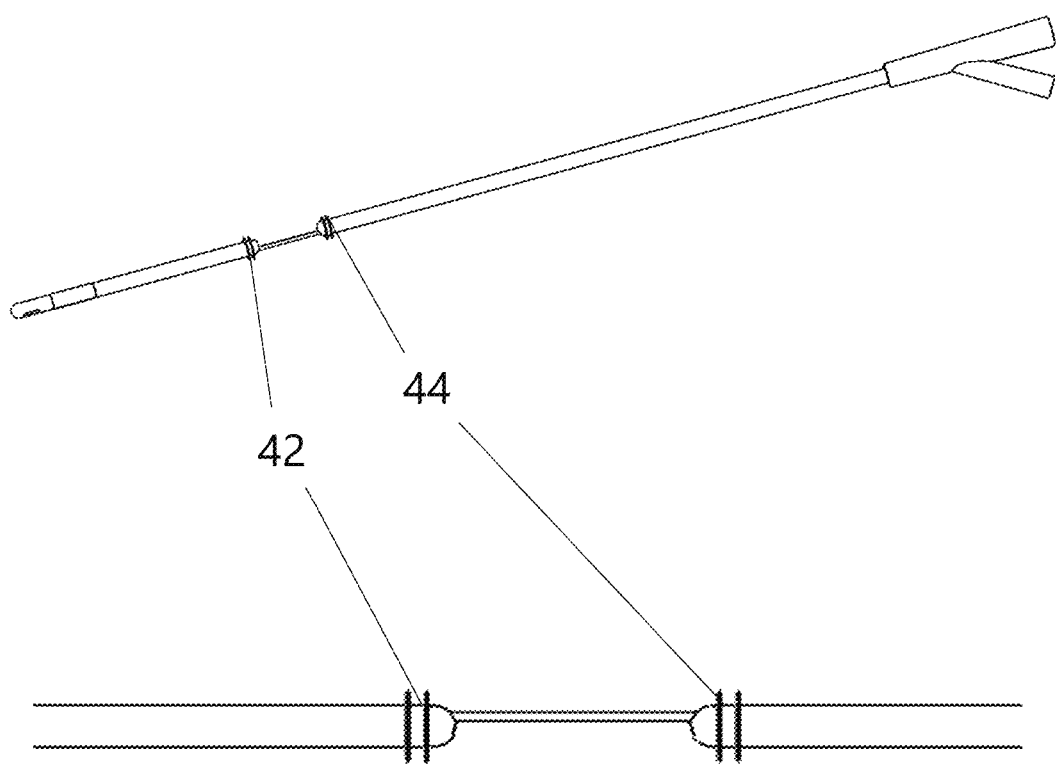
FIG. 14: illustrates possible locations of the obstruction element(s) in the form of pressure relief valves along various positions along the catheter device.

FIG. 14 shows another possible embodiment wherein the obstruction element 22 is in the form of two sets of gaskets 42 and 44 positioned around the edges of the proximal tube 6 and distal tube 8 respectively. The first set of gaskets 42 can be disposed around a region of the proximal tube 6 adjacent the buffer zone 12, and the second set of gaskets 44 can be disposed around a region of the distal tube 8 adjacent the buffer zone 12. The first set of gaskets 42 are shaped and dimensioned to direct any fluid, such as urine, downwards, and functions as a guide to direct/reflect any urine flowing out from the proximal tube 6 towards the distal tube 8. The second set of gaskets 44 are shaped and dimensioned to receive any flow urine around the buffer zone 12 into the urine lumen 14 of the distal tube 8. In some embodiments, the first gaskets 42 may be an inverted funnel, and the second set of gaskets 44 may be funneled shape, in use.

Figure 15:
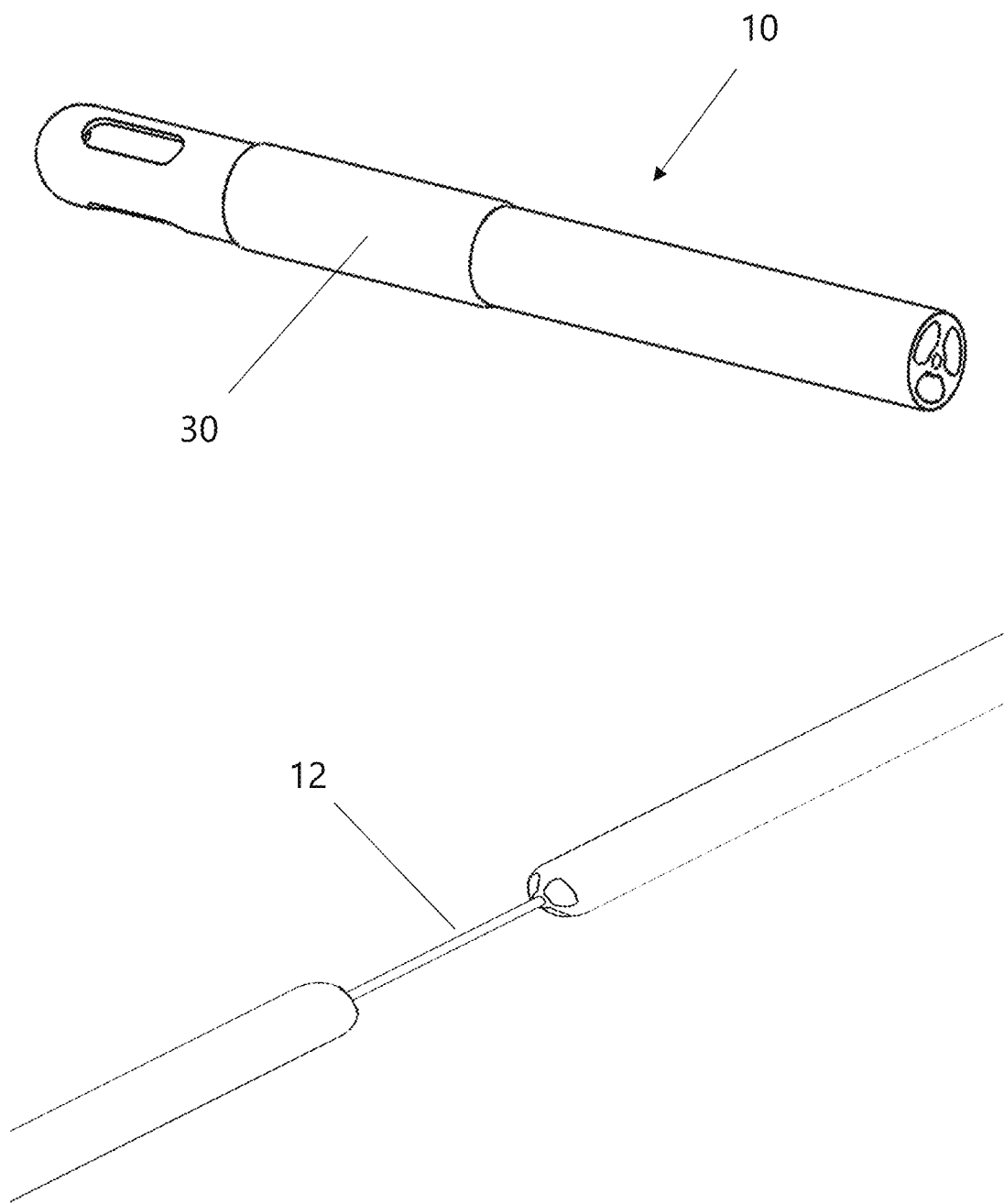
FIG. 15: illustrates another embodiment of the catheter device with multiple lumens for urine to flow therethrough.

FIG. 15 shows yet another embodiment of a catheter device 10, which shows a pen like device in an undeployed state. The buffer zone 12 of the catheter device 10 is similar to that of FIG. 10, wherein the second lumen 16 is in a coiled state which can be uncoiled. The buffer zone 12 is covered by a connector cover 30, and there may comprise sheaths 32 located around the proximal tube and the distal tube. It is to be appreciated that there comprises multiple first lumens or urine lumens arranged around the parameter of the proximal/distal tube. Each first lumen 14 is shaped like a fan extending from the center of the respective proximal/distal tube. At the center is the second lumen 16 which can be an inflation lumen to activate one or more obstruction element.

In various embodiments the inflation lumen 16 is made or coated with antibacterial materials. The inflation lumen 16 may further be coated with lubricants for improving effectiveness and for reducing friction during insertion/deployment.

In various embodiments the inflation lumen 16 is textured in a way which can inhibit the formation of biofilms. Other parts of the catheter device 10 can also be textured in a way which can inhibit the formation of biofilms.

In various embodiments an indicator in the form of a physical line connected with the distal tube end of the catheter. When deployed, the distal end moves outwards creating the buffer zone 12. The fixed indicator line would then be able to notify the user that the buffer zone 12 has been deployed sufficiently.

In various embodiments the sheath 32 is a removable sheath which covers the inflation lumen 16 in the retracted state such as a coiled state. This sheath 32 may be physically torn by pulling an attached line through the lumen. Or it could be torn by the opening of the buffer zone 12 from the first insertion configuration to the second retention configuration through the by longitudinal extension of the coiled inflation tube 16 when the two ends of the catheter are being pulled apart to expose the buffer zone.

In various embodiments the obstruction element 22 comprises an elastic portion 28 (see FIG. 3) of the proximal tube 6 surrounded by a noncompliant balloon expandable when fluid is added into the balloon to a predetermined pressure at which in presses on the elastic portion and occludes the proximal tube blocking urine from exiting the urinary bladder.

In various embodiments the obstruction element 22 in the form of one-way or multi-way valves can be opened and closed either manually or electrically operated, preferably in response to a predetermined feedback from a pressure sensor (not shown).

In various embodiments the urine flow obstruction element, may be any element configured to achieve to a temporary closure of urine flow and filling of the urinary bladder, such as a single or multiple clamps, valves, inflatable balloons. The flow obstruction elements may be incorporated at each point along the catheter. The flow obstruction elements can be operated manually or automatically to enable periodical filling and emptying of the urinary bladder configured to mimic biological bladder function.

In various embodiments an inflation lumen 16 is assembled onto the catheter device 10 and connector covers 30 by adhesives. The connector covers are made out of flexible and compliant material to prevent injury.

In some embodiments, the catheter device 10 comprises a flow sensor (not shown). The flow sensor may be arranged in network communication with an alert system for providing one or more alerts to medical practitioners in a case of catheter obstruction or poor urine flow.

The obstruction element is configured to build urine volume and pressure inside the bladder and void/flush it out periodically as required in manual or automatic way so the urine flushes out the bacteria both intra-luminally and extra-luminally from the urethra. While flushing as described, it preserves the bladder functionality for long term catheter usage (unlike regular Foley).

Obstruction elements in the catheter may support the clamp function and prevent urine leakage.

The buffer zone 12 provides true discontinuity i.e. its unique design is configured for comprehensive 360 degree flushing of the urethra walls by the voided urine.

In the described embodiments, the catheter device 10 provides for an area of discontinuity or buffer zone 12 so that urine can still flush comprehensively 360 degree of the urethra walls along the buffer zone.

In the described embodiments, the support element 18 is configured to provide mechanical support to the inflation lumen 16. The shape and structure is designed to establish the best support structure to enable the urine buffer zone to be successful.

The inflation lumen tube 16 is configured to provide continuity enabling inflation of the catheter. The optimal length of the urine buffer zone is preferably evaluated as the optimum result of the effect of urine flushing. The length of the urine buffer zone will have a direct impact on the length of the inflation lumen bridging tube.

In some embodiments, the length of the buffer zone may be between 1 millimeters (mm) to 40 mm, or 1 centimeters (cm) to 4 cm. As the length of the opening (buffer zone) affects the 'amount of flush' that pressurized urine passes through and at the same time the structural integrity of the device 10, a balance would have to be achieved between these two objectives.

In a pre-used state, the catheter device 10 may be properly sealed at the catheters 'buffer zone'. The structural strength of the catheter is sufficient for insertion and exertion of the catheter.

In the invention, part of the urine tube, that is inserted into the urethra will be eliminated and the two parts will be connected by a small diameter connection (that will be used to inflate the balloon inside the bladder). As shown in FIG. 1A, in buffer zone 12, the urine exits the proximal part of the urine tube and flow inside the urethra without any tube for about 20 mm. The urine flush any bacteria each time the urine valve is opened for flushing. The urine then enters the distal tube that is connected thought a urine valve to a standard urine collection bag.

In some embodiments, a valve is added configured to open the urine tube for draining the urine periodically (as required) so that the urine flow through the buffer zone can be significant and close to that found in normal, healthy person where the urine will flush the bacteria away from the urethra and at the same time keep the bladder expansion function. The valve is either manual or automatic operated.

The catheter of the present invention can be developed from biocompatible material, as used today for urine catheters and other urethra/bladder treatment materials.

Table 1 shows non-limiting examples of components used in the device 10. It is relevant to the catheter device 10 in the various embodiments.

TABLE 1

The components of various embodiments of the catheter device.

| Component | Material |
| --- | --- |
| Proximal and distal tubes | Latex (rubber) |
| | Silicon |
| | TPU |

TABLE 1-continued

The components of various embodiments of the catheter device.

| Component | Material |
| --- | --- |
| | PTFE |
| Inflation tube | Polytetrafluoroethylene (PTFE) |
| | Thermoplastic polyurethane (TPU) braided |
| | Polytetrafluoroethylene (PTFE) - pure/reinforced (braided, spring) |
| Coating on Inflation lumen/tube | Anti-microbial |
| | PTFE |
| | Silicone |
| | Hydrogel (can be hydrophilic or hydrophobic) |
| Connector cover | Thermoplastic polyurethane (TPU) |
| Glue | Ethyl adhesive (Loctite 4011) |
| | Cyanoacrylate |
| | Epoxy |
| | Polyurethane |
| Urine obstruction element | Clamp |
| | Valve |
| | Balloon |

Reference is made to FIGS. 10 and 11, illustrating an embodiment of a buffer zone, in respect to the present invention. In this embodiment the catheter enables urine flushing the urethra. In this embodiment the buffer zone 12 is supported by a single support structure which is also the inflation lumen 16 in which a fluid is pumped into the balloon to inflate it.

In this embodiment the inflation lumen 16 is rigid enough to transmit axial forces applied during the insertion of the catheter whilst being flexible and compliant enough to bend around obstacles and the natural curves of the urethra and bladder. The inflation lumen 16 is also sufficiently strong enough to withstand breakage, kinking and buckling under the normal forces found during intended use.

In this embodiment the inflation lumen 16 is assembled onto the catheter and connector covers by adhesives. The connector covers are made from flexible and compliant material to prevent injury. They also reduce friction by having small diameter tips that gradually increase to the diameter of the catheter.

Alternatively, in various other embodiments the buffer zone is also formed as a secondary action. In this embodiment, the catheter line appears continuous. The inflation tube is then elongated or stretched or slid out to enable an action step for deploying the buffer zone upon placing the catheter in position.

In this embodiment a sheath 32 or connector cover 30 surrounds the inflation tube in the initial configuration covering it to provide a smoother outer surface which is the same or close to the diameter of the catheter.

In this embodiment the sheath has a weak spot such as perforations or is weakly attached to one end of the catheter. This enables it to be released or break apart when the catheter is pulled forcibly apart, exposing the buffer zone by stretching the distance bridged by the inflation tube.

In this embodiment there is an indicator in the form of a physical line connected with the proximal part of the catheter. When deployed, the distal end moves outwards creating the buffer zone. The fixed indicator line is then able to notify the user that the buffer zone has been deployed sufficiently.

Alternatively, in various other embodiments there is a removable sheath which covers the coil. This sheath is physically torn by pulling an attached line through one of the lumen. Or it is torn by the opening of the void through the extension of the coiled inflation tube when the two ends of the catheter are pulled apart to expose the void.

Reference is made to FIGS. 10 and 9, illustrating a preferred embodiment of a buffer zone, in respect to the present invention.

In this embodiment the buffer zone 12 comprising the inflation lumen 16 and the support wires 18 is initially 25 millimeters (mm) then the connector covers are added to the distal tube and the proximal tube and the buffer zone is shortened to 15 mm. The connector covers make it easier to insertion the device into the urethra without damage to urethral cell tissue or to the buffer zone 12.

In this embodiment the soft rubber connector cover material and super elastic wire minimize injury during insertion.

In this wired embodiment the wires are able to support the urethral wall with minimal contact between the wires and the urethral wall as the connector covers have a larger diameter than the wire section in the buffer zone 12. Design of wire shape maximizes the effectiveness of urine flushing to clean it.

The wires are also for providing axial compressive strength to transmit the insertion force and prevent buckling.

Another aspect of the invention relates to a method of inserting the catheter device 10 into an individual including the steps of: anchoring the catheter device 10 in a urinary bladder via a retaining element, wherein part of the proximal tube is positioned within the urinary bladder; activating at least one obstruction element to restrict the flow of urine from the proximal tube to the area of discontinuity and to restrict the flow of urine from the area of discontinuity to the distal tube, thereby causing pressure build-up within the first lumen, and periodically deactivating the at least one obstruction element, thereby releasing the build-up urine within the first lumen to the area of discontinuity to achieve intra-luminal flushing and extra-luminal flushing.

Another aspect of the invention relates to a method of manufacturing the catheter device 10 comprising the steps of: creating an area of discontinuity or buffer zone; providing a support element at or around the buffer zone to provide structural rigidity; wherein the area of discontinuity comprises a support element configured to resist axial movement of the distal tube relative to the proximal tube and vice versa.

It should be further appreciated by the person skilled in the art that variations and combinations of features described above, not being alternatives or substitutes, may be combined to form yet further embodiments falling within the intended scope of the invention.

As would be understood by a person skilled in the art, each embodiment, may be used in combination with other embodiment or several embodiments.

Unless defined otherwise, all technical and scientific terms used herein have the same meaning as is commonly understood by a skilled person to which the subject matter herein belongs.

The invention claimed is:

1. A catheter device including
a proximal tube having a first part of a first lumen configured for urine to flow therethrough;
a distal tube having a second part of the first lumen configured for urine to flow therethrough;
a second lumen connecting the proximal tube and the distal tube; wherein an area of discontinuity is provided between the first part and second part of the first lumen; and
at least one obstruction element comprising a balloon positioned at a portion of the proximal tube for constriction of the proximal tube, and at least one obstruction element comprising one of the following: a valve and a clamp positioned at a portion of the distal tube for constriction of the distal tube, wherein the obstruction elements can thereby temporarily restrict the flow of urine through the area of discontinuity;
wherein the area of discontinuity comprises a support element configured to resist axial movement of the distal tube relative to the proximal tube and vice versa; and wherein the area of discontinuity includes an opening operable for urine to be flushed periodically out of the catheter.

2. The device of claim 1, wherein the at least one obstruction element is configured to periodically open to release urine, when present, at a predetermined pressure.

3. The device of claim 1, wherein the support element is integral with the second lumen.

4. The device of claim 1, wherein the support element comprises a plurality of elongated structures arranged to connect the proximal tube and the distal tube in a manner so as to provide structural rigidity at the area of discontinuity.

5. The device of claim 4, wherein the plurality of elongated structures are made of at least one of the following materials: nickel titanium, cobalt chromium, latex (rubber), TPU, PTFE.

6. The device of claim 1, wherein the second lumen is elastic and is extensible.

7. The device of claim 6, wherein the area of discontinuity is enclosed by a protective sheath, the protective sheath removable when the catheter device is deployed.

8. The device of claim 1, further comprising a plurality of first lumens.

9. The device of claim 1, wherein the second lumen is configured to allow a fluid to flow therethrough.

10. The device of claim 9, wherein the fluid is air.

11. The device of claim 1, wherein the length of the area of discontinuity is 0.1 centimeters (cm) to 4 cm.

12. The device of claim 1, wherein the proximal and/or distal tube is made of at least one of the following: —latex, silicon, Thermoplastic polyurethane (TPU), and Polytetrafluoroethylene (PTFE).

13. The device of claim 1, wherein the second lumen is made of at least one of the following: —PTFE, TPU.

14. The device of claim 13, wherein the second lumen is coated with anti-microbial, PTFE, silicone, or hydrogel.

15. The device of claim 1, wherein the length of the proximal tube is longer than the distal tube or vice versa.

16. A method of deploying the catheter device of claim 1 into an individual including the steps of:
anchoring the catheter device in a urinary bladder via a retaining element, wherein part of the proximal tube is positioned within the urinary bladder;
activating at least one obstruction element to restrict the flow of urine through the area of discontinuity, thereby causing pressure build-up within the first lumen, and periodically deactivating the at least one obstruction element, thereby releasing the build-up urine within the first lumen to the area of discontinuity to achieve intra-luminal flushing and extra-luminal flushing.

17. A method of manufacturing the catheter device of claim 1 comprising the steps of: creating an area of discontinuity or buffer zone; providing a support element at or around the buffer zone to provide structural rigidity; wherein the support element is configured to resist axial movement of the distal tube relative to the proximal tube and vice versa; and wherein the area of discontinuity includes an opening operable for urine be flushed periodically out of the catheter.

18. The device of claim 1, wherein the at least one obstruction element is configured to be activated by the second lumen to restrict the flow of urine.

\* \* \* \* \*